United States Patent
Lin et al.

(10) Patent No.: US 10,866,484 B2
(45) Date of Patent: Dec. 15, 2020

(54) LIGHT FREQUENCY UPCONVERSION OF LASER LIGHT, FOR CLEANSING

(71) Applicant: ABL IP HOLDING LLC, Conyers, GA (US)

(72) Inventors: Guan-Bo Lin, Reston, VA (US); David P. Ramer, Reston, VA (US); Yan Rodriguez, Suwanee, GA (US); Sean P. White, Reston, VA (US)

(73) Assignee: ABL IP HOLDING LLC, Conyers, GA (US)

( * ) Notice: Subject to any disclaimer, the term of this patent is extended or adjusted under 35 U.S.C. 154(b) by 153 days.

(21) Appl. No.: 16/121,002

(22) Filed: Sep. 4, 2018

(65) Prior Publication Data
US 2020/0073199 A1    Mar. 5, 2020

(51) Int. Cl.
| G02F 1/35 | (2006.01) |
| G02B 27/09 | (2006.01) |
| G02B 26/08 | (2006.01) |
| A61L 2/26 | (2006.01) |
| G02F 1/355 | (2006.01) |

(Continued)

(52) U.S. Cl.
CPC .......... *G02F 1/353* (2013.01); *A61L 2/0047* (2013.01); *A61L 2/10* (2013.01); *A61L 2/26* (2013.01); *G02B 26/0833* (2013.01); *G02B 26/101* (2013.01); *G02B 27/0955* (2013.01); *G02F 1/355* (2013.01); *G02F 1/3553* (2013.01); *A61L 2202/11* (2013.01); *A61L 2202/25* (2013.01);

(Continued)

(58) Field of Classification Search
CPC ..... G02F 1/353; G02F 1/355; G02B 27/0955; G02B 26/101; G02B 26/0833; A61L 2/26; A61L 2/10
See application file for complete search history.

(56) References Cited

U.S. PATENT DOCUMENTS

| 5,535,230 A | 7/1996 | Abe |
| 5,802,222 A | 9/1998 | Rasch et al. |

(Continued)

OTHER PUBLICATIONS

Khanikaev et al., Photonic Topological Insulators, Mar. 2013, Nature Materials, vol. 12, pp. 233-239 (Year: 2013).*

(Continued)

*Primary Examiner* — David P Porta
*Assistant Examiner* — Jeremy S Valentiner
(74) *Attorney, Agent, or Firm* — RatnerPrestia

(57) ABSTRACT

A cleansing lighting device includes a laser light source configured to emit light in the visible light spectrum or in the infrared light spectrum. The cleansing lighting device also includes a light frequency up-converter to convert longer wavelength light from the laser light source to shorter wavelength light. The converted light has a dominant wavelength in the portion of the ultraviolet range at or below 380 nm, suitable for the cleansing application. An example cleansing lighting device may also include an optical element, such as a beam shaping lens or a variable optical beam deflector, to distribute the resulting ultraviolet light from the up-converter for the cleansing application. Such a cleansing lighting device may be a standalone device, although the device or individual components for light-based cleansing may be incorporated in a luminaire, for example, together with an artificial light source adapted to general illumination.

18 Claims, 4 Drawing Sheets

(51) Int. Cl.
G02B 26/10 (2006.01)
A61L 2/10 (2006.01)
A61L 2/00 (2006.01)
(52) U.S. Cl.
CPC ........ *G02F 1/3551* (2013.01); *G02F 2202/30* (2013.01)

(56) References Cited

U.S. PATENT DOCUMENTS

| | | | |
|---|---|---|---|
| 6,393,038 | B1 | 5/2002 | Raymond et al. |
| 6,480,325 | B1 | 11/2002 | Batchko et al. |
| 6,736,517 | B2 | 5/2004 | Sherman et al. |
| 7,986,315 | B2 | 7/2011 | Sprague et al. |
| 9,136,673 | B2 | 9/2015 | Holder et al. |
| 2004/0217364 | A1 | 11/2004 | Tarsa et al. |
| 2005/0152421 | A1 | 7/2005 | Fujitani |
| 2006/0131695 | A1 | 6/2006 | Kuekes et al. |
| 2008/0180786 | A1 | 7/2008 | Bratkovski |
| 2011/0021970 | A1* | 1/2011 | Vo-Dinh ............ A61K 41/0042 604/20 |
| 2012/0106127 | A1 | 5/2012 | Hattori et al. |
| 2013/0177775 | A1* | 7/2013 | Cheah .................... B32B 7/12 428/480 |
| 2013/0329448 | A1 | 12/2013 | Franz et al. |
| 2014/0105784 | A1* | 4/2014 | Smeeton ............... B01J 19/123 422/24 |
| 2014/0341241 | A1 | 11/2014 | Essaian et al. |
| 2014/0353696 | A1 | 12/2014 | Kinoshita et al. |
| 2015/0085347 | A1 | 3/2015 | Choi et al. |
| 2016/0030610 | A1* | 2/2016 | Peterson .................. A61L 9/18 362/84 |
| 2018/0066810 | A1 | 3/2018 | Lentine et al. |

OTHER PUBLICATIONS

Kim et al., Extremely broadband topological surface states in a phonic topological metamaterial, Oct. 2019, Advanced Optical Materials, vol. 7, Iss. 20, pp. 1-8 (Year: 2019).*
Manuela Buonanno et al., "Germicidal Efficacy and Mammalian Skin Safety of 222-nm UV Light," Radiat Res. Author manuscript, Apr. 2017; 187(4): 483-491, 18 pages.
High Energy Ozone LLC—UV Sterilization Technology, "Technology for Improving Health," https://heo3.com, dated Mar. 8, 2018, 14 pages.
HEPACART Infection Control Technologies, Pathogen Reduction Box 3.0, HEPACART™, "The Pathogen Reduction Box Featuring Far-UV Sterilray," http://www.hepacart.com/pathogen-reduction-box-3.0, dated Aug. 8, 2018, 4 pages.
Airborne Pathogen Disinfection Module, The HEPACART® Airborne Pathogen Disinfection Module Featuring: Far-UV Sterilray Technology, http://www.hepacart.com/germbuster-air, dated Aug. 8, 2018, 5 pages.
OcularPD Index, Ocular PD LLC, "Germbuster-Eye," http://ocularpd.com, Copyright © 2018 Ocular PhotoDisinfection LLC, dated Aug. 8, 2018, 1 page.
HEPACART Infection Control Technologies, Far-UV STERILRAY™, http://www.hepacart.com/far-uv-sterilray, Copyright 2018, dated Aug. 8, 2018, 4 pages.
Pathogen Path Consulting LLC, "Air Surface and Liquid Disinfection," Patented Far-UV Sterilray Technology, http://www.far-uv.com/, dated Aug. 8, 2018, 5 pages.
Far-UV Sterilray—Superior UV Disinfection, "Far-UV Sterilray™ Technology," https://sterilray.com/, Copyright © 2017—Far-UV Sterilray, dated Aug. 18, 2018, 14 pages.
United Crystals, "Non-linear Optical Crystal Overview," https://unitedcrystals.com/NLOCOverview.html, © 2016 United Crystals, dated Aug. 7, 2018, 2 pages.
James Johnson, "Selection of Materials for UV Optics," Dec. 1, 2008, OPTI 521, pp. 1-6.
Wikipedia, "Ultraviolet germicidal irradiation," https://en.wikipedia.org/wiki/Ultraviolet_germicidal_irradiation, dated Jan. 25, 2018, 9 pages.
United Crystals, "Properties of KDP, DKDP and ADP Crystal," https://unitedcrystals.com/KDPProp.html, © 2016 United Crystals, dated Jul. 16, 2018, 2 pages.
Kavita Devi et al., "Tunable, continuous-wave, ultraviolet source based on intracavity sum-frequency-generation in an optical parametric oscillator using BiB3O6", © 2013 Optical Society of America, Oct. 12, 2013, vol. 21, No. 21, Optic Express pp. 24829-36, 8 pages.
Wikipedia, "Sum-frequency generation," https://en.wikipedia.org/wiki/Sum-frequency_generation, dated Jul. 16, 2018, 2 pages.
Wikipedia, "Optical frequency multiplier," https://en.wikipedia.org/wiki/Optical_frequency_multiplier, dated Jul. 16, 2018, 1 page.
Wikipedia, "Acousto-optic Modulator," https://en.wikipedia.org/wiki/Acousto-optic_modulator, dated Aug. 8, 2018, 4 pages.
Brimrose Corp., "Free Space Acousto-Optic Modulators," https://www.brimrose.com/acousto-optic-modulators, dated Mar. 8, 2018, 6 pages.
Wikipedia, "Second-harmonic generation," https://en.wikipedia.org/wiki/Second-harmonic_generation, dated Jul. 16, 2018, 10 pages.
Guoqiang Shi, et al., "Finding the Next Deep-Ultraviolet Nonlinear Optical Material: NH4B4O6F," ACS Publications, © American Chemical Society, J. Am. chem. Soc. 2017, 139, pp. 10645-10648, 4 pages.
Zhi Fang, et al., "Deep-Ultraviolet Nonlinear Optical Crystal Cs2Al2(B3O6)20: A Benign Member of the Sr2Be2(BO3) 2O Family with [Al2(B3O6)2O]2—Double Layers," Chem. Eur. J. 10.1002/chem.201801742, first published Apr. 15, 2018, 8 pages, https://doi.org/10.1002/chem.201801742.
Min Luo, et al., "M2B10O14F6 (M = Ca, Sr): The First Two Noncentrosymmetric Alkaline-Earth Fluorooxoborates as Promising Next-Generation Deep-Ultraviolet Nonlinear Optical Materials," J. Am. Chem. Soc., Just Accepted Manuscript, DOI: 10.1021/jacs.8b01263, publication date Mar. 8, 2018, downloaded from http://pubs.acs.org on Mar. 3, 2018, ACS Publications, © American Chemical Society, 6 pages.
J.X. Wang et al., "Recent progress of research on III-nitride deep ultraviolet light-emitting diode," (in Chinese). Sci Sin-Phys Mech, Astron, 2015, 45: 067303, doi: 10.1360/SSPMA2015-00026, Sci. Sin-Phys. Mech. Astron, 2015, 21 pages.
Sunil Mittal et al., "Topological Photonic Systems," May 2018, Optics & Photonics News, pp. 37-43, 7 pages.
Behrooz Semnani, et al., "Graphene-Integrated Plasmonic Structure for Optical Third Harmonic Generation," IEEE Journal of Selected Topics in Quantum Electronics, vol. 23, No. 1, Jan./Feb. 2017, 12 pages.
Nils Weber et al., "Double resonant plasmonic nanoantennas for efficient second harmonic generation in zinc oxide," Physical Review B 95, 205307 (2017) © 2017 American Physical Society, 6 pages.
Sheng Liu et al., "Resonantly Enhanced Second-Harmonic Generation Using III-V Semiconductor All-dielectric metasurfaces," Nano Letters 2016, 16(9) pp. 5426-5432, Publication Date Aug. 8, 2016, Copyright © 2016 American Chemical Society, https://pubs.asc.org/doi/abs/10.1021/acs.nanolett.6b01816, 30 pages.
Chawin Sitawarin, et al., "Inverse-designed photonics fibers and metasurfaces for nonlinear frequency conversion [Invited]," B82, vol. 6, No. 5, May 2018, Photonics Research, 2018, 8 pages.
Cheng Wang et al., "Ultrahigh-effciency second-harmonic generation in nanophotonic PPLN waveguides," arXiv:1810.09235 [physics.app-ph], Sep. 24, 2018, 5 pages.
Non Final Office Action for U.S. Appl. No. 16/259,225, dated Apr. 17, 2020, 24 pages.
MIT Technology Review, "The Danger of Green Laser Pointers," Jan. 16, 2019, downloaded fro https://www.technologyreview.com/s/420214/the-danger-of-green-laser-pointers/, 3 pages.
David P. Ramer et al., U.S. Appl. No. 16/259,225, filed Jan. 28, 2019, entitled "Light Frequency JP-Conversion of Laser Light, for Producing Green or Yellow Light," 45 pages.
Notice of Allowance for U.S. Appl. No. 16/259,225, dated Aug. 25, 2020, 14 pages.

* cited by examiner

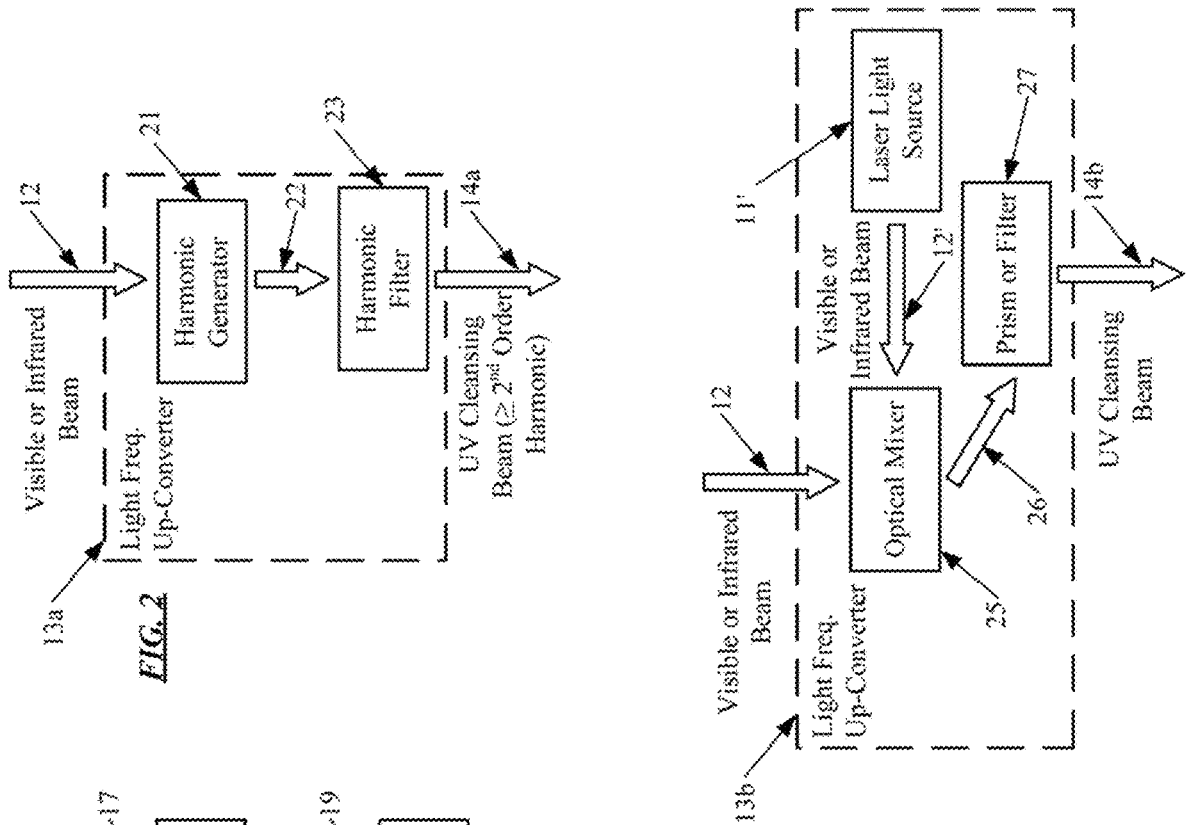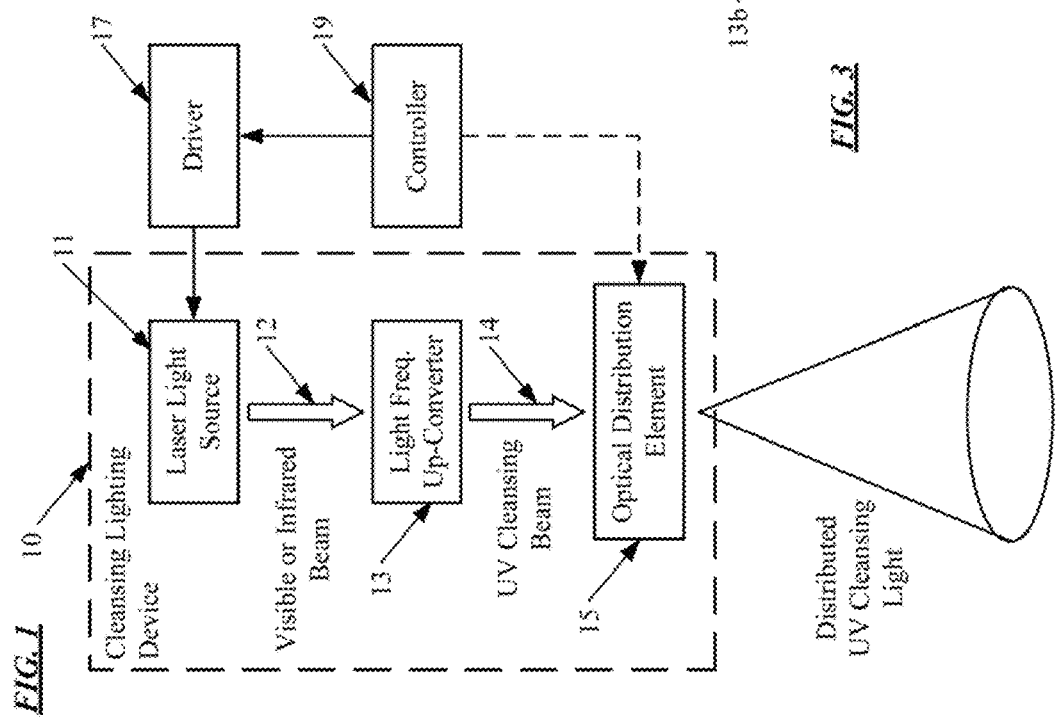

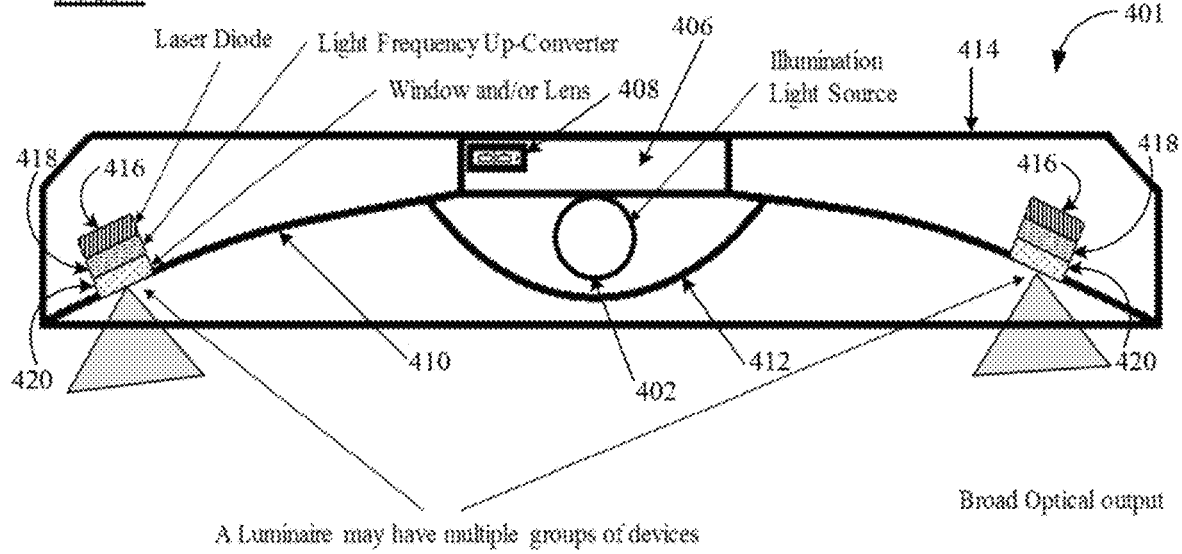
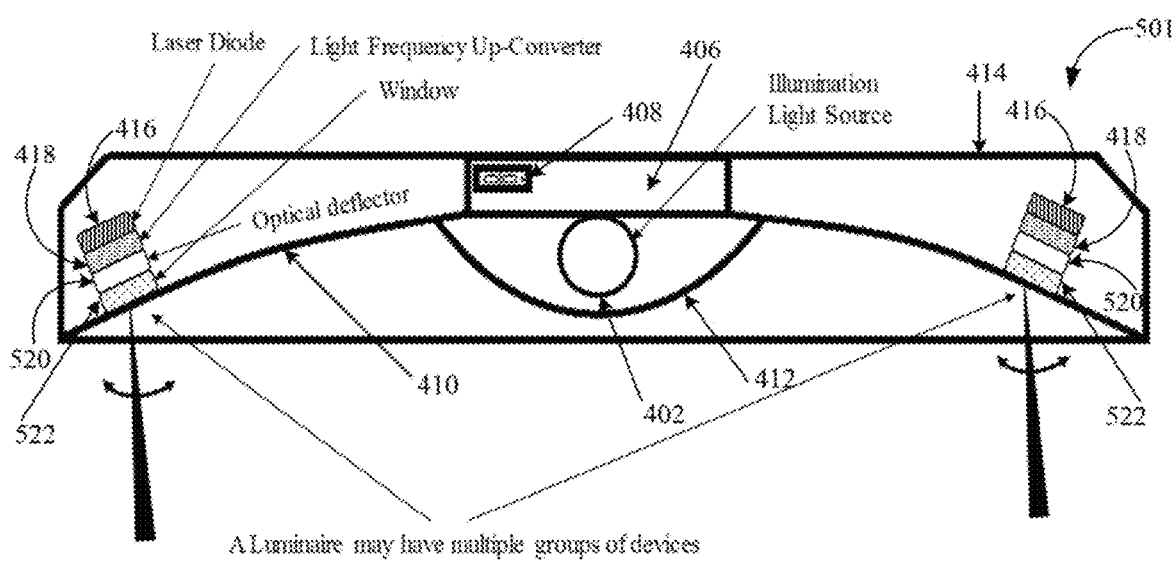

US 10,866,484 B2

LIGHT FREQUENCY UPCONVERSION OF LASER LIGHT, FOR CLEANSING

TECHNICAL FIELD

The present subject matter relates to cleansing lighting devices, luminaires incorporating cleansing lighting components and techniques of operating such equipment to provide ultraviolet light in a suitable wavelength range to deactivate a pathogen for a cleansing application, e.g. for sanitation or sterilization.

BACKGROUND

In recent years, there have been various proposals to incorporate, in general lighting equipment, light sources specifically configured to deactivate bacteria on a surface, such as Methicillin-Resistant Staphylococcus Aureus (MRSA) on work surfaces, sinks, floors etc. of hospitals, nursing homes or the like. A number of these proposals have suggested use of cleansing light at or around 405 nm, that is to say, in the near-ultraviolet end of the visible spectrum.

Ultraviolet (UV) light also is known to deactivate various types of pathogens. However, it is difficult to efficiently generate light in shorter wavelength regions of the UV portion of the spectrum.

SUMMARY

The cleaning examples discussed below therefore utilize a laser light source of a fairly efficient type for generating long wavelength light and a light frequency up-converter to obtain UV light of wavelengths suitable for deactivating a pathogen.

An example of a cleansing lighting device includes a laser light source configured to emit laser light having a dominant wavelength in the visible light spectrum or in the infrared light spectrum. A light frequency up-converter is coupled to convert the laser light emitted by the laser light source to ultraviolet light having a dominant wavelength in the ultraviolet spectrum at or below 380 nm. An optical element coupled to the light frequency up-converter distributes the ultraviolet light, for a cleansing application in a volume in the vicinity of the lighting device.

The cleansing lighting device may be implemented as an individual unit or incorporated into other types of equipment commonly found in location that may benefit from light-based deactivation of potentially harmful pathogens. In many of the detailed examples, the elements of the cleansing lighting device are included as parts of a luminaire.

An example luminaire includes a general illumination light source capable of emitting visible light for a general illumination application in a volume in the vicinity of the luminaire. The luminaire also includes a laser light source configured to emit laser light having a dominant wavelength in the visible light spectrum or in the infrared light spectrum. A light frequency up-converter is coupled to convert the laser light emitted by the laser light source to ultraviolet light having a dominant wavelength in the ultraviolet spectrum at or below 380 nm. The luminaire in this example further includes an optical element coupled to the light frequency up-converter to distribute the ultraviolet light for a cleansing application in the volume in the vicinity of the luminaire.

In some examples, the light frequency up-converter is a harmonic generator configured to convert the laser light to a second or higher order harmonic light having the dominant wavelength in the ultraviolet spectrum at or below 380 nm.

In other examples, the light frequency up-converter includes an additional light source and an optical mixer coupled to the two light sources and configured to mix light from the laser light sources to produce the ultraviolet light.

Additional objects, advantages and novel features of the examples will be set forth in part in the description which follows, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out in the appended claims.

BRIEF DESCRIPTION OF THE DRAWINGS

The drawing figures depict one or more implementations, by way of example only, not by way of limitations. In the figures, like reference numerals refer to the same or similar elements.

FIG. 1 is a high level functional block diagram example of a cleansing lighting device and some drive/control components.

FIG. 2 is a high level example of a light frequency up-converter using a harmonic generator.

FIG. 3 is a high level example of a light frequency up-converter using an additional laser and an optical mixer.

FIG. 4 is a cross-sectional view of an example of a luminaire with light-based cleansing components, in this example, with a window and/or lens for dispersion of the cleansing light from each of two sources/up-converters.

FIG. 5 is a cross-sectional view of another example of a luminaire with light-based cleansing components, in this example, with a variable optical beam deflector for scanning of the cleansing light from each of two sources/up-converters.

DETAILED DESCRIPTION

Figure 6:
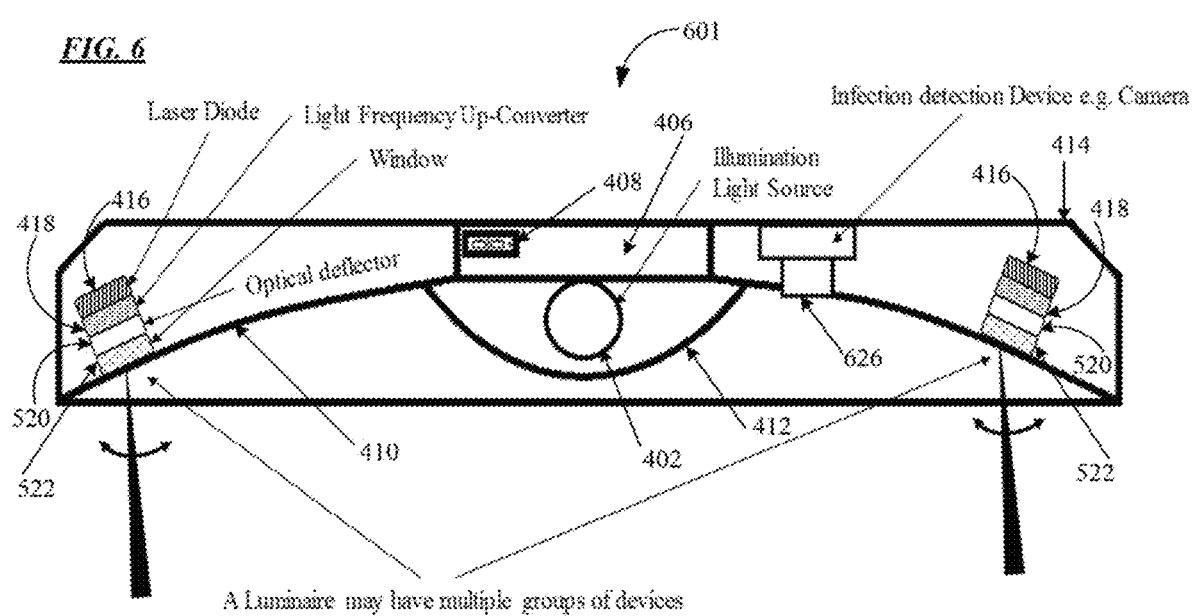
FIG. 6 is a cross-sectional view of a further example of a luminaire similar to the luminaire of FIG. 5, but also having a camera or other sensor for detecting potentially infectious materials or locations for light-based cleansing.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The various examples disclosed herein relate to a lighting devices for cleansing application, e.g. for sterilization or sanitation, and to luminaires incorporating general illumination light sources as well as components for such cleansing. The light produced for cleansing has properties (e.g. wavelength, energy and/or time duration) suitable to deactivation of one or more potentially harmful pathogens. In the examples, lasers provide light for cleansing via a frequency up-conversion (conversion higher frequency and this to shorter wavelength) to produce light of a wavelength suitable for the cleansing application.

For example, a cleansing lighting device includes the laser light source configured to emit light in the visible light spectrum or in the infrared light spectrum and a suitable light frequency up-converter. An example cleansing lighting device may also include an optical element to distribute the resulting ultraviolet light from the up-converter for a cleansing application. Such a cleansing lighting device may be a standalone device, although in many of the detailed examples below, components for light-based cleansing are incorporated in a luminaire, for example, together with an artificial light source adapted to general illumination.

Pathogens, for example, include micro-organisms, bacteria, viruses, protozoa, prions, funguses and other infectious agents. Such a pathogen is deactivated, for example, if the cleansing light exposure kills the pathogen or otherwise damages the pathogen (e.g. ruptures the cell membrane or breaks DNA or RNA chain in the pathogen) so as to limit or prevent the harmful function of the pathogen.

The term "luminaire," as used herein, is intended to encompass essentially any type of device that processes energy to generate or supply artificial light, for example, for general illumination of a space intended for use of occupancy or observation, typically by a living organism that can take advantage of or be affected in some desired manner by the light emitted from the device. However, a luminaire may provide light for use by automated equipment, such as sensors/monitors, robots, etc. that may occupy or observe the illuminated volume or space, instead of or in addition to light provided for the benefit of an organism. However, it is also possible that one or more luminaires in or on a particular premises have other lighting purposes, such as signage for an entrance or to indicate an exit. In most examples, the luminaire(s) illuminate a volume, space or area of a premises to a level useful for a human in or passing through the volume or space, e.g. general illumination of a room or corridor in a building or of an outdoor space such as a street, sidewalk, parking lot or performance venue. The actual source of general illumination light in or supplying the light for a luminaire may be any type of artificial light emitting device, several examples of which are included in the discussions below. Each example of luminaire with integrated cleansing capability described later includes a laser light source and a frequency up-converters and may include an optical distribution element.

Terms such as "artificial lighting," as used herein, are intended to encompass essentially any type of lighting in which a device produces light by processing of electrical power to generate the light. An artificial lighting device, for example, may take the form of a lamp, light fixture, or other luminaire that incorporates a light source, where the light source by itself contains no intelligence or communication capability, such as one or more light emitting diodes (LEDs) or the like, or a lamp (e.g. "regular light bulbs") of any suitable type. The illumination light output of an artificial illumination type luminaire, for example, may have an intensity and/or other characteristic(s) that satisfy an industry acceptable performance standard for a general lighting application.

The term "coupled" as used herein refers to any logical, optical, physical or electrical connection, link or the like by which signals or light produced or supplied by one system element are imparted to another coupled element. Unless described otherwise, coupled elements or devices are not necessarily directly connected to one another and may be separated by intermediate components, elements or communication media that may modify, manipulate or carry the light or signals.

Light output from a cleansing lighting device or a luminaire may carry information, such as a code (e.g. to identify cleansing lighting device, the luminaire or the location of the device or luminaire) or downstream transmission of communication signaling and/or user data. The light based data transmission may involve modulation or otherwise adjusting parameters (e.g. intensity, color characteristic or distribution) of the cleansing light and/or the illumination light output.

Reference now is made in detail to the examples illustrated in the accompanying drawings and discussed below. Several of the drawings, e.g. FIGS. 1 to 3, use block arrows to represent light beams. The direction of the arrows in the drawings, however, are for ease of illustration only. In actual implementations of cleansing lighting devices or luminaires, the beams may be aimed in a variety of different directions, to facilitate optical processing by the various components discussed herein and/or to direct the cleansing output light in a manner suitable to a particular application or installation. Also, the drawings show light outputs from the example cleansing lighting devices and luminaires in a downward direction, for example, as if mounted to direct output light down from a ceiling, pedestal or lamp post through an illuminated volume toward a floor or a work surface positioned above the floor. It should be apparent that a cleansing lighting device or luminaire may be positioned in a variety of other orientations suitable to cleansing of a particular space or surface area and/or for desired artificial general illumination.

FIG. 1 includes a high level functional block diagram illustration of an example of a cleansing lighting device 10. The cleansing lighting device 10 includes a laser light source 11. Although other types of sources may be used, the examples utilize one or more laser diodes to provide a laser beam of light represented by the block arrow 12 from the source 11 in the drawing. The laser light emitted as shown at 12 has a dominant wavelength in the visible light spectrum or in the infrared light spectrum. For example, the visible spectrum is from approximately 390 nm to around 700 nm, and the infrared spectrum is from approximately 700 nm to around 15,000 nm. Hence, in the example, the laser light emitted as shown at 12 has a dominant wavelength in the range from approximately 390 nm to approximately 15,000 nm.

Examples of suitable laser diodes for implementing the laser light source 11 include edge emitting laser (EEL) diodes of suitable wavelengths and vertical cavity surface emitting laser (VCSEL) diodes of suitable wavelengths. For luminaires, particularly those using LED based light sources, it may be more convenient to integrate lasers into the luminaires by using one or more VCSEL type laser diodes because that type of laser diode uses a packaging arrangement that is similar to the packages of LEDs used today in luminaires. It should be understood, however, that these examples are non-limiting and that other types of laser diodes or other laser devices may be used to implement the source 11.

The cleansing lighting device 10 in the example includes a light frequency up-converter 13 coupled to receive the beam 12 from the laser light source 11. The light frequency up-converter 13 is configured to convert the laser light 12 emitted by the laser light source 11 to ultraviolet (UV) light having a dominant wavelength in the ultraviolet spectrum at or below 380 nm. The beam output by the light frequency up-converter 13 is shown diagrammatically by the arrow 14. The UV dominant wavelength and possibly the spectral power distribution of the beam 14 around that wavelength are chosen by optimizing the design of the light frequency up-converter 13 for a particular cleansing application. Examples of suitable light frequency up-converters are described in more detail later.

Light in a range from 180 nm to 420 nm may be efficacious in that it deactivates harmful microscopic organisms (e.g. certain viruses and bacteria) upon exposure of the microscopic organisms to an appropriate dosage of such light. Light of wavelengths in a portion of this range, particularly UV light below about 380 nm, is often difficult to generate efficiently using LEDs and other traditional light sources. The laser and up-conversion approach addresses this difficulty in generating suitable UV light in the range below about 380 nm.

The ultraviolet light in beam 14, for example, may have its dominant wavelength in a range of from 180 nm to 380 nm. Light nearer the low end of that wavelength range has been found to have little or no adverse effect on human skin or eyes. Hence, the ultraviolet light, for example UV cleansing light beam 14, may have its dominant wavelength in a range of from 200 nm to 225 nm. A narrower range for effective cleansing and minimal harmful side effects on humans may utilize UV light with a dominant wavelength in a range of from 207 nm to 222 nm.

UV-C light, particularly in the range of 207 nm to 222 nm, has a number of advantages for cleansing applications over other types of UV light. Such cleansing light does not penetrate human skin, and it does not penetrate the human cornea. Hence, use of UV-C light in the 207 nm to 222 nm range for cleansing applications is expected to have little or no harmful effect on human occupants if present during a cycle of cleansing of a space with such light. Also, light in this range is effective with respect to a larger variety of pathogens, including influenza. Furthermore, light in the 207 nm to 222 nm range is more effective and can deactivate pathogens using shorter exposure times than say light in higher-wavelength UV or near-UV visible light. Effective dosages of 405 nm near-UV cleansing light may require hours of exposure. Light in the in the range of 207 nm to 222 nm range, for example, may kill harmful bacteria with exposure times less than a minute, in some examples, around 5 secs. Such a limited requirement for exposure duration may enable effective sanitation of a space during even short periods when the space is unoccupied. Even if occupied, the short period of cleansing lighting further reduces potential for adverse impact on humans.

The cleansing lighting device 10 in the example also includes an optical distribution element 15. The optical element 15 is coupled to the light frequency up-converter 13 to receive the light beam 14 having the wavelength(s) intended to deactivate one or more potentially harmful pathogens. The element 15 distributes the ultraviolet light, for a cleansing application in a volume in the vicinity of the lighting device 10. In the drawing, the cone represents the distributed output of the optical distribution element 15 as the output light passes through a volume and may impact a surface represented by the oval. If an appropriate dosage of such output light exposes a pathogen in the air or on the surface, the organism is deactivated by the light exposure. The proper dosage of cleansing light for a particular pathogen is a function of the exposure intensity and the length of time (duration) of the exposure to the cleansing light. Also, some pathogens may be more susceptible to UV light of different wavelengths and/or power distribution.

The example in FIG. 1 includes a driver 17 and a controller 19. The cleansing lighting device 10 may incorporate one or both of the driver 17 and the controller 19, or the driver 17 and the controller 19 may be separately located and coupled to the components of the device 11 by appropriate power and/or control links. The controller 19 may be a simple device such as an ON/Off switch, which also serves as a user interface. The controller may be (or be responsive to) a sensor, e.g. an occupancy sensor. Another alternative is to implement the control functions using a programmable control system, an example of which is described later relative to FIG. 7. When activated for sanitation or sterilization, circuitry used to implement the driver 17 supplies operational power, for example of suitable current and/or voltage, to turn ON the laser light source 11. The driver 17 may convert power from any suitable source, e.g. battery or more likely main lines power, to the power to drive the particular type of laser device(s) used to implement the laser light source 11.

The driver 17 and thus the laser light source 11 are at least controllable with respect to ON/OFF state of the laser light output of the source 11. Depending on the implementation of the source 11 and the driver 17, it may also be possible to vary one or more characteristic(s) of light output of the source 11, for example, to adjust output light intensity and/or to tune the dominant wavelength and possibly the spectral power distribution of the laser light output. The various controllable operational characteristics or states of the driver 17 and thus the laser light source 11 are controlled by the controller 19. Although a purpose-built logic and circuitry arrangement may be used, in most examples, the controller is implemented using a micro-control unit (MCU) or a microprocessor (µP) as the main logic or intelligence of the controller 19. The controller 19 controls the driver 17 and thus the laser light source 10 to manage the ON/OF timing and any variable characteristic(s) of the laser light output of the source 11 and thus of the cleansing light output from the optical distribution element 15 to achieve a suitable exposure dosage to deactivate one or more types of pathogens in the space or on a surface intended to be cleansed or sterilized.

Examples of the optical distribution element 15 providing beam shaping or providing beam steering are discussed in more detail later. Several of the examples of element 15 are passive, e.g. passive lenses or the like. Other examples of element 15, such as variable beam deflectors for scanning, may be electrically controllable. Hence, in the example of FIG. 1, an option is for the controller 19 to be coupled (as shown by the dashed-line arrow) to also control operation of the optical distribution element 15.

The light frequency up-converter 13 may be implemented by a variety of different technologies. Although other types of up-converters may be used or developed in future, two general types of up-converters will be discussed by way of non-limiting examples. One general category of suitable light frequency up-converters generates light of a frequency harmonic (frequency is an integer multiple of the laser frequency) and thus having a corresponding shorter wavelength. The second general category of suitable light frequency up-converters discussed herein uses an additional laser and an optical mixer to generate a higher frequency (shorter wavelength) cleansing light.

FIG. 2 is an example of a light frequency up-converter 13a using a harmonic generator 21. The higher frequency harmonic output beam 22 exhibits an inversely smaller wavelength. For example, generation of a second order harmonic (frequency doubling) results in harmonic light having a dominant wavelength that is half the dominant wavelength of the original laser light; generation of a third order harmonic (frequency tripling) results in harmonic light having a dominant wavelength that is one-third the dominant wavelength of the original laser light; and so on for higher order harmonics.

Generation of a second order harmonic of a laser beam involves two photons of the same frequency interacting via a nonlinear optical material. The nonlinear processing via the material optically combines the two photons so as to create one new output photon. The output photon has approximately twice the energy of one original photon (combines energy from the two received/original photons). The resulting higher energy photon has a frequency approximately twice that of the original photons and thus approximately half of the light wavelength of the original photons. Similarly, generation of a third order harmonic of a laser beam involves three photons of the same frequency interacting via a nonlinear optical material. The nonlinear processing via the material optically combines the three photons so as to create one new output photon. The output photon has approximately three-times the energy of one original photon (combines energy from the three received/original photons). The resulting higher energy photon has a frequency approximately three-times that of the original photons and thus approximately one third of the light wavelength of the original photons.

Similar techniques may generate fourth and still higher order harmonics. Alternatively, higher frequency/shorter wavelength harmonics may be generated by stacking nonlinear materials forming a multiple-harmonic generator, e.g. two successive second order harmonic generators to produce output light approximately one fourth the wavelength and approximately four times the frequency of the original laser photons.

For example, for cleansing applications, if 207 nm cleansing light is desired for a particular application and the laser source 11 provides ~414 nm light, then a second order harmonic implementation of the converter 21 produces ~207 nm light. Similarly, if the laser provides ~621 nm light, then a third order harmonic implementation of the converter 21 produces ~207 nm light; and if the laser provides ~828 nm light, then a fourth order harmonic implementation of the converter 21 produces ~207 nm light; and so on. By way of other examples, if the laser provides ~405 nm light, then a second order harmonic implementation of the converter 21 produces 202.5 nm light; and if the laser provides ~850 nm light, then a converter implementation that provides a second order harmonic and then provides a further similar conversion again can provide 202.5 nm light.

There are a number of types of available nonlinear materials that may be tailored to convert available laser light to harmonics suitable to generating UV light for cleansing. Two general categories of suitable materials are nonlinear crystals and nonlinear metamaterials, although other types of nonlinear materials may be suitable. The two non-limiting categories of materials are discussed in somewhat more detailed below.

In one example category of nonlinear materials, the harmonic generator is formed a nonlinear crystal material. The chemical and crystalline properties of the material can be chosen/controlled during manufacture to obtain the desired harmonic generation between a particular input beam (e.g. of a particular dominant wavelength) and a harmonic having a dominant wavelength in a desired range suitable for deactivation of pathogens.

Example nonlinear crystals are birefringence crystals. Such a crystal has two different refractive indexes along two axes of the crystal. The fundamental laser beam 12 is focused and put through along a first optical axis of the nonlinear crystal. The incident laser beam 12 is separated into two different paths, one path having the fundamental wavelength of the input beam 12 while the other path performs n-order harmonic generation which meets a particular phase match condition.

Nonlinear crystal material, for example, may be manufactured from: ammonium dihydrogen phosphate (ADP), lithium triborate (LBO), lithium tantalate (LT), lithium niobate (LN), potassium dihydrogen phosphate (KDP), deuterated KDP (DKDP), potassium titanyl phosphate (KTP), beta barium borate (BBO), Lithium Iodate (LiIO3), AgGaS2, AgGaSe2, KNbO3 or the like. Traditional methods to manufacture a nonlinear crystal of properties for generating the n-order harmonic tailored to a particular wavelength range for the laser beam 12 from a particular laser light source 11 involve material selection and appropriate control of pressure, temperature, etc. during the crystal growth process. The manufacturing technique, however, may create uncertainty as to conformance of resulting crystals to design parameters, the manufacturing process is time-consuming, and such crystals have limited nonlinear efficiency based on the nature of the materials used to form the crystals. Nonlinear crystals, the applicable materials and the procedures for crystal growth are fairly mature technologies utilized for other types of light processing applications. Once a recipe is found for crystal formation suitable for a particular conversion desired for a cleansing application, those nonlinear crystals could be fairly inexpensive solutions.

In another example category of nonlinear materials, the harmonic generator is formed of a nonlinear metamaterial. The nonlinear metamaterial may be a photonic crystal or other type of metamaterial; and the nonlinear metamaterial is of type/structure configured to exhibit: (a) resonance for frequency of light from the laser light source and resonance for the light of the second or higher order harmonic; (b) substantial mode overlap between the frequency of light from the laser light source and harmonic frequency of the light of the second or higher order harmonic; and (c) intrinsic nonlinear material or phase matching. Examples of suitable photonic crystal metamaterials include nonlinear metamaterials having an all dielectric cylinder structure and topological metamaterials. Other examples of suitable nonlinear materials include metamaterials having a gold split resonator structure or a gold cross bar structure.

The nonlinear metamaterials, for example, can be made by nanoscale three-dimensional (3D) printing, nanoimprinting, or photolithography. Such manufacturing techniques are less time consuming than crystal growth. The techniques for making nonlinear metamaterials also provide better control of the structure during manufacturing, which thereby enables efficient tailoring of the material structure to a particular application, in this case, conversion from a particular beam frequency/wavelength to the harmonic frequency/wavelength selected for the cleansing application. The nonlinear metamaterial approach also has other advantages over the nonlinear crystals in that the manufacturing techniques allow for design of material permeability, permittivity, and/or susceptibility of the harmonic generator 21, according to size, material, and geometry of the nonlinear metamaterial. Use of the nonlinear metamaterial also enables tighter field confinement and higher field enhancement due to resonance, which provides more efficient frequency mixing.

Returning to the discussion of the example of FIG. 2, the beam 22 will include the intended harmonic and may include some other light components, such as a remnant of light of the original dominant wavelength and frequency and/or other harmonics of the source beam 12. Hence, the example light frequency up-converter 13a may also include a filter 23 to pass the desired harmonic and block other light outside a defined bandpass region around the intended dominant harmonic wavelength. As a result of the filtering, the light output beam 14a will predominantly include cleansing light of a spectral power distribution around the particular harmonic intended for deactivation of pathogens. Alternatively, prism may be used to separate the energy in the beam 22 and to direct only the appropriate n-order harmonic out as beam 14, 14a to the distribution element 15.

In the harmonic type conversion example, the harmonic generator 21 produces a selected second or higher order ($\geq 2^{nd}$ order) harmonic. The particular harmonic is selected by selection of the material and/or structure of the harmonic generator 21. The output cleansing light at 14a after filtering is UV cleansing light having wavelengths in the bandpass region around the particular second or higher order ($\geq 2^{nd}$ order) harmonic dominant wavelength.

FIG. 3 is an example of a light frequency up-converter 13b that utilizes an optical mixer 25 to produce the UV cleansing beam 14b having the dominant wavelength in the range intended for deactivation of pathogens.

In general, a mixer is a device that receives two input signals and outputs a mixed signal. The mixed output signal may have a frequency that is the sum of the frequencies of the input signals, or the mixed signal output signal may have a frequency that is the difference of the frequencies of the input signals. An up-converter utilizes a mixer configured to output a signal having a frequency that is the sum of the frequencies of the input signals. For applications in radio-frequencies and microwave frequencies, for example, mixers are implemented in the form of appropriate electronic circuitry. For light, a mixer for up-conversion may be implemented utilizing a material configured to have appropriate optical properties in the relevant light spectrum bands of the expected inputs and the desired output.

The optical mixer 25 in light frequency up-converter 13b is a material configured to perform a sum-frequency change function, for example, a form of optical frequency mixer configured to receive and mix photons of light of two different frequencies from two different sources. The material effectively combines two photons of different frequencies into one photon of higher energy and thus higher frequency and shorter wavelength. Rather than a doubling of frequency as in the second order harmonic generator 21, the optical mixer 25 produces a higher energy photon having a frequency corresponding approximately to a sum of the frequencies of the two original input photons. The example assumes a sum-frequency conversion for light of two beams of different frequencies. It should be understood, however, that similar techniques may be used that combine light of three or more beams of different frequencies to effectively sum the frequencies and produce corresponding shorter wavelength light.

The optical mixer 25 in the example therefore receives two input signals in the form of light beams 12, 12' from the two laser sources 11, 11', and the optical mixer 25 outputs the result of the mixing of the two input light signals 12, 12' as a higher frequency light beam 26. The light beam 26 has a shorter wavelength inversely proportional to the sum of the higher frequencies of input light beams 12, 12'. The laser diode(s) or the like forming the laser light source 11 supply light beam 12 to one input of the optical mixer 25. The light frequency up-converter 13b uses a second laser light source 11' to supply the beam 12' to the optical mixer 25. Although other types of laser devices may be used as source 11', in most examples, the second laser light source 11' is formed by one or more laser diodes structurally similar to the diode(s) forming examples of laser light source 11. The laser diode(s) of the second laser light source 11' produce light 12' of frequency and dominant wavelength different from the frequency and dominant wavelength of laser light 12 output by the laser diode(s) of the first laser light source 11. The optical mixer produces higher energy photons in beam 26 of higher frequency and thus shorter wavelength(s).

The beam 26 from the optical mixer 25 will include frequency components formed by the mixing function of the optical mixer 25 and may include some remnant(s) of either one or both of the light beams 12, 12' from the laser light sources 11, 11'. Hence, the example light frequency up-converter 13b may also include a prism or filter 27 to output light at 14b that is in a range around a frequency/wavelength suitable for deactivation of one or more pathogens. The prism or filter 27 in the example of FIG. 3 may be similar to the filter 23 and/or the alternative prism discussed earlier relative to FIG. 2. As a result of the band selection by the prism or filter, the light output beam 14b will predominantly include cleansing light of a spectral power distribution around a dominant wavelength intended for deactivation of one or more pathogens. The frequency of the UV cleansing light 14b in this example is essentially a sum of the frequencies of the laser light of beams 12, 12'; and the dominant wavelength of the light 14b is approximately the inverse of the sum of the frequencies of the laser light of beams 12, 12'.

There are a number of available metamaterials that may tailored to mix laser light to generate frequency-sum beam 26 in the optical mixer 25 of the up-frequency converter 13b. Second harmonic generation, as in one of the harmonic examples discussed above relative to FIG. 2, is a special case of frequency-sum-generation by an optical mixer. In a device for second harmonic generation, both photons that are combined to form the new higher frequency (shorter wavelength harmonic) have the same frequency. As a result, the output photon has double the input frequency and half the wavelength. The optical mixer 25 may be formed of nonlinear crystal material or nonlinear metamaterial similar to such materials above described for a second harmonic generation version of generator 21. Although a nonlinear metamaterial similar to one of the metamaterials discussed above for the harmonic generator may be used to implement the optical mixer 25, in an example, the optical mixer 25 is a nonlinear crystal. The type of nonlinear crystal may be based on one of the earlier discussed crystal materials, such as LBO. Another example of a nonlinear crystal for use as the optical mixer 25 is crystalline bismuth triborate (BIBO).

The lasers and nonlinear crystal or metamaterials forming the optical mixer may be configured to provide phase matching between the input laser beams 12, 12' as well as with the resulting output beam 26. For a nonlinear metamaterial implementation, the inputs on the nonlinear metamaterial that received beams 12, 12' from the laser light sources 11, 11' may be configured to provide resonance at the respective frequencies of the laser beams 12, 12'. The output surface on the nonlinear metamaterial forming the optical mixer 25 may be configured to provide resonance at the intended frequency of the output beam 14b. The metamaterial may also provide a substantial mode overlap between the frequency of light of the output beam 14b and each of the frequencies of the beams 12, 12' from the laser light sources 11, 11'.

FIGS. 4 to 6 are cross-sectional views of several examples of luminaires that incorporate laser and frequency up-conversion elements for cleansing. For convenience, some basic components and components for general artificial illumination as well as a couple of the cleansing components that are the same in these three examples, are indicated by the same reference numbers in the three drawings and will be discussed first. The examples differ with regard to aspects of the cleansing light distribution elements and/or include an extra detection device, as will be discussed individually with regard to the respective drawings.

Each of the example luminaires 401, 501 and 601 in FIGS. 4 to 6 includes a general illumination light source 402. The source 402 may be any light source used for artificial illumination. Examples include conventional lamps such as incandescent, halogen, halide or florescent lamps. Examples also include various solid state lighting devices. Most solid state based luminaires today use some number of light emitting diodes (LEDs).

As illustrated, each of the example luminaires 401, 501 and 601 in FIGS. 4 to 6 includes a reflector 410 and a diffuser 412 optically coupled to the output of the light source 402. The reflector 410 and the diffuser 412 may at least partially enclose the light source 402, as illustrated by way of example in these drawings. The reflector 410 and the diffuser 412 distribute the light from the source 402 in a volume or on an area intended for illumination, in accordance with a distribution specification for the particular luminaire configuration. A wide variety of materials and structures may be used to implement the reflector 410 and the diffuser 412. The location and optical relationship of the reflector 410 and the diffuser 412 relative to the source 402 and to each other are shown by way of non-limiting examples only; and it should be apparent that other arrangements may be suitable to particular artificial illumination applications. Also, depending on the particular general illumination application of a luminaire and/or the aesthetics of the luminaire design, one or both of the reflector 410 and the diffuser 412 may be omitted.

The examples assume a relatively 'smart' luminaire implementation having communication capability for control of the general illumination and/or cleansing capabilities of the example luminaires 401, 501, 601. Hence, these examples also include an access area 406 for wired communication connectors, such as RJ45 connectors 408. If the luminaire incorporates wireless communication capability, connectors 408 and the access area 406 may be omitted. Power connections to AC mains or to DC lines to a separately located driver may also be provided in the access area 406 or elsewhere on the luminaire 401, 501 or 601.

In the examples of FIGS. 4 to 6, each of the luminaires 401, 501 and 601 also includes a housing 414. The housing may have any particular structure and/or aesthetic design that is suitable to the intended location, intended mounting, illumination application specifications, and cleansing functions.

As illustrated, each of the example luminaires 401, 501 and 601 in FIGS. 4 to 6 includes cleansing components for UV light cleansing of the type described herein. Cleansing light may be provided from one location on the luminaire, two locations (as shown by way of example) on the luminaire, or from more locations on the luminaire. The exact locations may vary to conform to the structure of the luminaire and the intended field of cleansing light distribution for a particular luminaire product configuration.

Hence, in the example luminaires 401, 501 and 601, each luminaire includes two laser diodes 416 forming two laser light sources, such as any of the laser light sources discussed above relative to the examples of FIGS. 1 to 3. Each such luminaire also includes a light frequency up-converter 418 coupled to receive the beam from a respective one of the laser diode type sources 416. Each light frequency up-converter 418 is configured to convert the laser light to UV light, of dominant wavelength (and possibly spectral power distribution) suitable for a cleansing application as described herein. The light frequency up-converters 418 in example luminaires 401, 501 and 601 may be formed like any of the light frequency up-converters discussed above relative to the examples of FIGS. 1 to 3.

FIG. 4 shows the luminaire 401 wherein each set of the light-based cleansing components has a window and/or lens 420 coupled to the output of the light frequency up-converter 418 for passively dispersing the cleansing light. A window would close an opening through the reflector 410 to prevent entry of contaminants into the interior of the luminaire 401 and may provide some dispersion, e.g. the material of the window may be selected to diffuse UV light or may be coated with a diffusing material. A lens typically would be formed of a suitable optical material that is transparent in the relevant UV wavelength range but shaped to provide a desired distribution angle output. A lens may provide more efficient dispersion of the cleansing light over a desired two-dimensional angular range of emission; although if the lens does not completely fill the opening through the reflector 410, a transparent or translucent window may be provided (in combination with the lens) to cover or close off the opening and prevent entry of contaminants into the interior of the luminaire 401. The material of the window and/or lens 420 may be selected to withstand the effects of long term exposure to UV light in the range utilized for the cleansing application of the luminaire 401. For example, the window and/or lens 420 may be formed of a suitable quartz glass for a luminaire that emits UV-C light, particularly for light having a dominant wavelength in the range of 207 nm to 222 nm. Fused silica (or quartz, SiOx) is a transparent material in the ultraviolet (UV) range and is commonly used to form UV optics. Other common UV optics materials include calcium fluoride ($CaF_2$), magnesium fluoride ($MgF_2$), and sapphire (aluminum oxide, $Al_2O_3$). The transmittance of such materials usually is above 80% for light in the 200 nm to 380 nm range.

FIG. 5 illustrates a luminaire 501 with light-based cleansing components similar to those of FIG. 4, except that the luminaire 501 includes a variable optical beam deflector 520 in place of each of the windows/lenses 420 of luminaire 401. Hence, in the example luminaire 501, each set of the light-based cleansing components has an optical deflector 520 coupled to the light frequency up-converter 418 for actively scanning the cleansing light over a desired output angular range. For further discussion, we will assume laser point sources and two-dimensional scanning by the optical deflectors 520. It should be appreciated that other arrangements may be utilized, such as rows of lasers and up-converters, with the up-converters in each row coupled to a one-dimensional line scanning type variable optical deflector.

Returning to the example using laser point sources, e.g. laser diodes with individual up-converters and deflectors, the deflector hardware used to implement the scanning provides two-dimensional beam scanning. Each such optical deflector 520, for example, may include a mirror mounted for controlled tilt around two axes or motion and a microelectromechanical system (MEMS) for moving the mirror about both axes. A beam directed at the mirror is scanned in two dimensions as the mirror cyclically changes angular orientation around each of the two axes of motion. In such an optical deflector 520 for cleansing, the MEMS can adjust the deflection range and timing, in response to control signals, to adjust the distribution of the cleansing light output.

Such an optical deflector 520 may be similar to MEMS based beam deflectors utilized in LIDAR devices for laser based ranging and detection applications. For cleansing purposes, however, the reflective surface of the mirror of each optical deflector 520 would be formed of a suitable material to reflect light in the particular UV wavelength range output by the light frequency up-converter 418 and to be relatively impervious to long term exposure to such UV light.

The MEMS mirror type device is given by way of a non-limiting example of an implementation of the optical deflector 520, although other devices may be used. A few other examples include a galvo mirror scanner, a liquid-crystal polarization grating, an optical antenna/phased array, an acoustic beam steering device, or the like.

A window 522 may be provided to cover each aperture through the reflector 410 for cleansing lighting output, in luminaire 501, so as to prevent entry of contaminants into the interior of the luminaire 501. If provided in this beam steering example, the window would be transparent 522. Each window 522 may be made of a material similar to the material of the windows in the earlier example of FIG. 4, except that in the luminaire 501 with beam deflection, the window 522 need not provide any passive dispersion of the beam.

FIG. 6 shows a luminaire 601 having the general illumination components and the cleansing components 416, 418 similar to those of the luminaires of FIGS. 4 and 5. The luminaire 601 includes a detection device 626. The luminaire 601 could use a window or lens to disperse the cleansing light as shown at 420 in FIG. 4, for example, where the detection device 601 merely detection a condition such as occupancy/non-occupancy to trigger operations of the light source 402 or the laser diode(s) 416. For discussion and illustration purposes, the luminaire 601 uses optical deflectors 520 similar to those in the luminaire 501 of FIG. 5. The use of the variable optical deflectors 520 allows control of the direction of the cleansing line beam to areas or locations selected or identified in response to sensing by the detection device.

The example luminaire 601 therefore includes a camera or other sensor as the detection device 626 for use in controlling light-based cleansing operations. The detection device, for example, may detect presence of a pathogen in the air or on a surface of an area about the space or volume served by the luminaire 626 to trigger or direct the cleansing lighting output(s) from the luminaire 601. By way of another sensing example, a camera type detection device 636 might allow a controller of the luminaire 610 to identify locations in the area serviced by the luminaire 601 where occupants passing through or using the space may have touched exposed surfaces creating points of likely contamination. Such detection might be used to control one or more of the optical deflectors 520 to direct the cleansing light to apply a dosage of the UV cleansing light at the identified location(s).

The example luminaires of FIGS. 4 to 6 included only one type implementation of the cleansing components. Although there were two sets, in FIG. 4, each set of cleansing components used a window or lens 420. Similarly, although there were two sets of cleansing components, in FIGS. 5 and 6 both sets included beam deflectors 520. It should be appreciated that a given luminaire may include combinations with different components, for example, one set with a window or lens and another set with an optical deflector. In another example luminaire, one set of cleansing components may have a first combination of laser diode and light frequency up-converter, and another set of cleansing components in the luminaire may use a different laser diode and/or a different light frequency up-converter.

Figure 7:
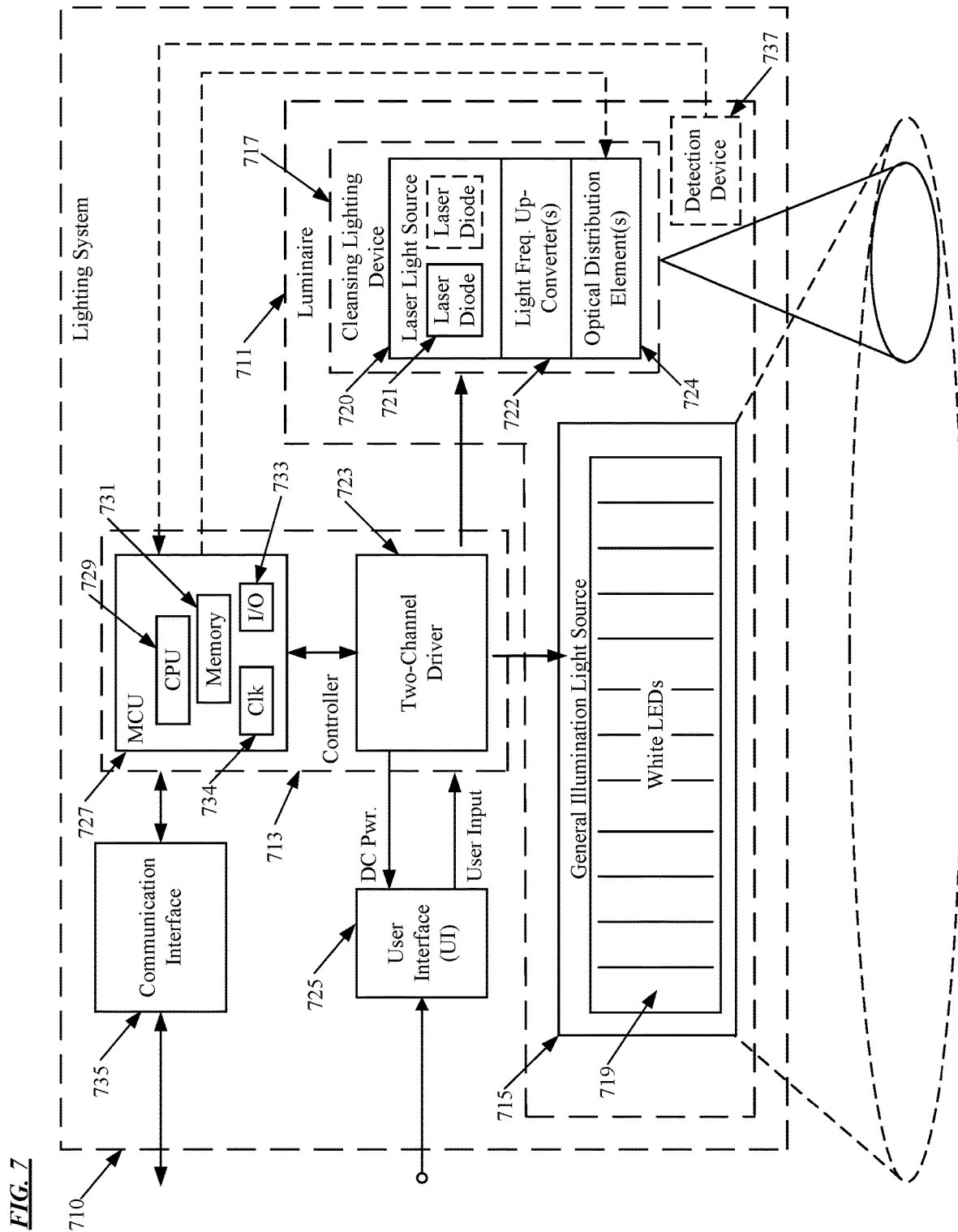
FIG. 7 is a high level functional block diagram example of a lighting system, which includes a luminaire having components of the device of FIG. 1 together with a general illumination light source, where the system also includes circuit elements to operate the general illumination light source and to operate the components of the luminaire.

FIG. 7 is a high level functional block diagram example of a relatively intelligent implementation of a lighting system 710, which includes a luminaire 711, a controller 713 and components similar to those of the cleansing device of FIG. 1. Simpler implementations, for example, with a switch as the user interface and controller and without an interface for communication with other systems or equipment are contemplated.

With specific reference to the example of FIG. 7, the components for the cleansing related features/functions of the luminaire 711 may be somewhat separately located and optically coupled as may be appropriate. In the illustrated example, however, the components for the cleansing related features/functions are elements of a cleansing lighting device 717 incorporated in the luminaire 711. Although the drawing shows only one cleansing lighting device 717, the luminaire 711 may include two or more cleansing devices 717.

The luminaire 711 includes a white light type source 715, for general illumination. A variety of different types of light sources may be used to implement the white light source 715. In the example, the white light source utilizes an appropriate number of white LEDs 719 of a type and number typically used for general illumination, e.g. a sufficient number and LEDs to provide overall light intensity and possibly other light characteristics suitable for a traditional white light indoor or outdoor illumination application. The cleansing lighting device 717 of the luminaire 711 has a laser light source 720, for example, including one or more laser diodes 721 of any of the types discussed relative to the earlier examples for emitting laser light in the visible or infrared spectrum (e.g. from about 390 nm to about 15,000 nm).

The cleansing lighting device 717 in the FIG. 7 example includes a light frequency up-converter 722 coupled to receive each beam from the diode(s) 721 of the laser light source 720. The light frequency up-converter 722 is configured to convert the laser light emitted by the laser light source 720 to ultraviolet (UV) light having a dominant wavelength in the ultraviolet spectrum at or below 380 nm. The UV dominant wavelength and possibly the spectral power distribution around that wavelength of the beam output by the light frequency up-converter 722 may be chosen by optimizing the design of the light frequency up-converter 722 for a particular cleansing application. The light frequency up-converter 722 may be implemented as discussed above with respect to the examples of FIGS. 2 and 3.

The cleansing lighting device 717 in the example also includes an optical distribution element 724, which may be implemented as in any of the earlier examples of FIGS. 1 to 6. The optical element 724 is coupled to the light frequency up-converter 722 to receive the light beam output from the light frequency up-converter 722, having the wavelength(s) intended to deactivate one or more potentially harmful pathogens. The optical distribution element 724 distributes the ultraviolet light, for a cleansing application in a volume in the vicinity of the luminaire 711.

In the drawing, the solid-line cone below the cleansing lighting device 717 represents the distributed output of the optical distribution element 724 as the output light passes through a volume and may impact a surface represented by the solid-line oval. If an appropriate dosage of such output light exposes a pathogen in the air or on the surface, the organism is deactivated by the light exposure. Although shown as a small cone in only a portion of a larger area illuminated by the general illumination source 715 (shown by way of example in dotted lines), the optical distribution element 724 may be configured to distribute the cleansing UV light over more or all of the area illuminated by the general illumination source 715. Alternatively, the luminaire 711 may include a suitable number of cleansing lighting devices 717 to provide the cleansing UV light over more or all of the area illuminated by the general illumination source 715.

The controller 713 is coupled to the light sources 715, 720 of the luminaire 711 to control light emission from the white light source 715 and light emission from the laser light source 720. The controller 713 controls at least the ON/OFF states of the white light source 715 and the laser light source 720. The controller 713 may also control one or more other characteristics of operation of each of the light sources 715, 720 of the luminaire 711, such as intensity of light output from each source, color characteristic(s) of white light output or frequency and wavelength tuning of the UV cleansing light output.

In the example of FIG. 7 each source 715 or 720 includes a number of LEDs 719 or 721, and the controller 713 utilizes a two-channel LED driver. Any two-channel LED driver 723 that provides sufficient controllable power to drive the selected LEDs 719 and 721 may be used. Examples of suitable drivers 723 are available from eldoLED B.V. One of the control channel outputs of the driver 723 in connected to drive the LEDs 719 of the white light source 715, and the other of the control channel outputs of the driver 723 is connected to drive the LEDs 721 of the laser light source 720. Alternative implementations of the sources 715, 720 may have additional types of LEDs, e.g. an RGBW implementation of source 715 may have four types of independently controllable LEDs, for red (R), green (G), blue (B) and white (W). In another example, the laser light source 721 may have a sufficient number of laser diodes or groups thereof in the same or a different cleansing device in the luminaire to provide separate controllable outputs, in which case the driver would provide corresponding additional output channel(s) as appropriate. In such implementations of the luminaire 711, the driver 723 may be of a type having additional control channels for the additional types of LEDs or laser diodes. The driver implementations with two or more channels, however, are discussed here by way of non-limiting examples only; and it should be understood that an appropriate number of drivers of appropriate types may be separately provided for the white LEDs 719 of the general illumination light source 715 and/or the laser diodes 712 in one or more cleansing lighting devices 717 included in a luminaire 711.

Although not shown, the two channel driver 723 may receive power from AC mains, 7100V AC to 488V AC, e.g. 120V AC or 220V AC. The driver 723, for example, may be a multi-volt input device capable of driving the LEDs using power obtained from any AC source in a range of 120V AC to 227V. It is also possible to implement the luminaire 711 with low voltage DC power supply, such as a 24V supply that hospitals utilize for magnetic resonance imaging (MRI) rooms in which ferromagnetic materials may not be permitted in the room with the MRI devices. As another alternative, the luminaire may use a battery power source, as an alternative or a backup to AC mains power. The circuitry of the device 710 may be located remotely from the luminaire 711, so that only the sources 715, 720 are included in the luminaire 711, and one or more remotely located drivers would connect to the LEDs 719, 721 to supply controlled current to drive the LEDs 719, 721.

The driver 723 in the example is directly responsive to an input from a user interface device 725 and exchanges data with a processor, which in the example is a microcontroller unit (MCU) 727 although a microprocessor or other type of processor circuitry may be used. In an implementation using an eldoLED driver as driver 723 of the system 710, the driver may supply DC power to the user interface device 725. The user interface device 725 may be a simple switch, a dimmer, a keypad, touchpanel etc. In other implementations using different types of drivers, the MCU 727 may receive input from the user interface device 725 and control the driver 723 based on the received inputs (rather than the user inputs going to the driver 723).

Depending on the implementation of the user interface 725, the controller may be configured to respond to an input received via the user interface 725, for example, to adjust one or more of: ON/OFF state of the cleansing light emission from the cleansing lighting device 717, ON/OFF state of the white light emission from the white light source 715, intensity of the white light emission from the white light source 715, and/or color characteristic(s) of the white light emission from the white light source 715. The configuration(s) of the controller, the driver and the laser diodes may support other types of control of the cleansing light. Examples of such additional controllable aspects of the cleansing light device operation include (but are not limited to): frequency/wavelength tuning, variable intensity, or pulsing with various controlled parameters. The additional control of any such aspects of the UV cleansing light emissions could be controlled in response to user input but often would be controlled in accordance with an algorithm programmed into the controller 713. For the algorithmic control approach, however, a user with suitable privileges, such as an administrator, may be able to input some parameters of the control algorithm via the user interface 725 or more likely via a convenient user terminal device (not shown) and communication through a network and the communication interface 735.

In some examples, the optical distribution element 724 is a passive optical device, such as a beam shaping (e.g. spreading) lens or a diffuser. In other examples, the optical distribution element 724 is a variable optical beam deflector, similar to a device used in an optical beam scanner. A variable beam scanner is a controllable device; and with such an implementation of the optical distribution element 724, the controller 713 would also control one or more aspects of operation of variable optical beam deflector. For example, the controller 713 typically would activate and deactivate the deflector of element 724 when the controller 713 activates and deactivates the laser light source 720 for overall operations (not necessarily with high-low state transitions of any laser pulse operations). The controller 713 may also control parameters of the scanning operation of the deflector of element 724, for example, to target a specific area or areas for cleansing.

In an LED based implementation of the luminaire 711, the LEDs 719 and the LEDs 721 may be mounted on one or more circuit boards housed within the luminaire 711. For example, the LEDs 719 and the LEDs 721 may be mounted at appropriate locations on one circuit board, for example. The luminaire 711, however, may have separate circuit boards for the LEDs 719 of source 714 and the LEDs 721 of one or more cleansing lighting devices 717. The particular circuit board configuration, for example, may be adapted to the desired form factor of the luminaire 711, to optimize heat dissipation from the LEDs and/or to provide cleansing UV outputs from cleansing lighting device(s) 717 at locations selected to provide optimal coverage of the area or space illuminated and cleaned by the lighting system 710.

An MCU like that shown at 727 typically is a microchip device that incorporates the actual processor circuitry in the form of a central processing unit (CPU) 729 along with various memories 731 for storing instructions for execution by the CPU 729 as well as data having been processed by or to be processed by the CPU 729, and input/output ports (I/O) 733 for suitable connection/communication of the MCU 727 with other system elements. The example MCU also implements a clock (Clk) 734 for timing related functions. The clock 734 may be a specific circuit within the MCU 721 or implementing as a program controlled function of the CPU processor 729.

The CPU, any circuitry of the clock, the memory and the I/O of the MCU 727 typically are all included on a single chip and sometimes referred to as a "system on a chip" or SoC. Although shown separately, the elements of the MCU 727 may be incorporated on a chip with the two-channel LED driver 723 and/or with circuitry of a network communication interface 735. The memory 731 for example, may include volatile and non-volatile storage; and the program instructions stored in the memory 731 may include a lighting application (which can be firmware), in this example, for implementing the processor functions of the controller 713 relating to controlling the white light output and cleansing light output from the luminaire.

The example represents an arrangement in which one controller controls a single luminaire 711. As shown in FIG. 7, the luminaire 711 provides both general illumination and cleansing light in a room or other space. The lighting system 710, however, may be easily modified to include and control a larger number of such luminaires.

For example, the LED driver 723 (FIG. 7) may be expanded to provide two controlled drive channel outputs to the LEDs of the sources in each of one or more additional luminaires 711. In the example, the driver 723 is in the controller 713, which may be separate from the luminaire 711. In an alternate approach for unified processor control of a larger number of luminaires 711, each luminaire may include a two-channel LED driver, and one MCU or the like may control two or more such driver-integrated luminaires. It should also be apparent that the driver and MCU of the controller 713 and possibly the communication interface 735 may be implemented within the luminaire 711.

The communication interface 735 may be any communication device suitable for lighting related local communications between the system 710 and other similar systems, with common control equipment such as wall controllers or on-premises servers or gateway, or even with an external wide area network (WAN). The communication interface 735, for example, may be a network access card supporting wired connectivity over a data network, such as Ethernet, or may be a wireless transceiver compatible with a standardized wireless communication protocol, such as WiFi, Zigbee, personal area network (PAN) e.g. in the 900 MHz band, Bluetooth or Bluetooth Low Energy (BLE), LiFi, etc.

Network communications, for example, may allow operation of a neighboring number of luminaires 711 for each of some number of zones in a large space, in a coordinated way to implement cleansing and illumination procedures. Some areas of the zone would have overlapping exposure from two or more luminaires 711, e.g. between adjacent luminaires or in the center of the area, whereas other areas of the zone around the periphery may have little or no overlapping exposure and receive light only from one of the luminaires. In such a scenario, the network communications allows the MCU or MCUs that control the luminaires 711 of a particular zone to adjust operations of the various cleansing lighting devices 717, e.g. to optimize cleansing light uniformity as much as feasible while insuring that all areas of the zone receive at least the minimum amount for the intended disinfection dosage.

Pathogens are sensitive to an overall applied energy of the cleansing light. The overall energy is a function of both intensity and accumulated exposure time. Stated another way, pathogens are effected by both a cumulative time duration of exposure to the cleansing light and the amplitude or level of the cleansing light exposure. For example, if cumulative exposure time of 1 with an average exposure amplitude 10 over that timeframe kills the exposed bacteria, it is reasonable to assume that an exposure of amplitude 5 kills the exposed bacteria after exposure for a cumulative exposure time of 2, or that exposure of amplitude 20 kills the exposed bacteria after exposure for a cumulative exposure time of 0.5 (units of time and exposure are omitted for convenience).

The controller 713 in the example at least can control ON/OFF state of the laser light source(s) 720 and thereby vary the overall duration of emissions, and the controller 713 may control laser emission intensity and thereby control intensity of emitter UV cleansing light. Some implementations also allow tuning of the frequency/wavelength of the UV cleansing light, either by tuning the laser 721 of the primary laser light source or by tuning an additional laser implemented in an up-converter that utilizes an optical mixer (see discussion of FIG. 3). The controller 713 in the example may also control scanning area and frequency, if the element 724 supports beam scanning. Alternatively or in addition, if the system 710 supports pulsing of laser emission, then the controller 713 may control frequency, time duration or width, phase or the like of the pulses of UV cleansing light output by each cleansing lighting device 717. Such parameters of the UV cleansing light are controlled to achieve an average energy of the emitted UV cleansing light over a period of time, e.g. to achieve dosage of the cleansing light sufficient to deactivate a bacteria or other pathogen within a distribution area for the emission after passage of defined period of time for an overall cleansing cycle.

Returning to FIG. 7, output of one or both of the light sources 715, 717 may be adjusted or otherwise controlled in response to one or more sensed conditions. Sensors for use in controlling the general illumination light source 715, such as occupancy sensor, color temperature detectors, and/or ambient light level sensors may be used, but are omitted from the drawing for convenience.

For purposes of controlling cleansing operation by one or more cleansing lighting devices 717 in the luminaire 711, the example system 710 of FIG. 7 also optionally includes one or more detection devices 737. The detection device 737 is shown in the luminaire 711, similar to the example of FIG. 6; although the detection device 737 may be located separately but in the general vicinity of the luminaire 711. In some implementations of luminaires or in implementations of standalone cleansing lighting devices, it may be advantageous to integrate the detection device with the components forming the cleansing lighting device.

The detection device 737 may be a camera or other sensor that provides information to the MCU 727 of the controller 713 for analysis of a condition that may be useful in control of cleansing operations of the cleansing lighting device(s) 711. Such sensing, for example, may detect presence of a pathogen in the air or on a surface of an area about the space or volume served by the luminaire 711. The controller 713 might then respond to such detection by operating the cleansing lighting device(s) 711 in the luminaire 711 for a suitable cleansing cycle to apply a dosage of the UV cleansing light sufficient to likely deactivate the pathogen.

By way of another sensing example, a camera type detection device 737 may allow the MCU 727 of the controller 713 to identify locations in the area serviced by the luminaire 711 where occupants passing through or using the space may have touched exposed surfaces creating points of likely contamination. Again, the controller 713 might respond to such detection by operating the cleansing lighting device(s) 711 in the luminaire 711 for a suitable cleansing cycle, but in this case, control scanning by a variable beam deflector to apply a dosage of the UV cleansing light at the identified location(s).

Other types of sensors may be used instead of or in addition to the camera in the above examples; and other responsive control strategies may be implemented using equipment like that of the system 710. For example, timing of cleansing operations may be based at least in part on sensing of occupancy. Also, with the network communications capability, results of sensing by the detection device 737 and/or instructions for responsive controlled cleansing operations may be communicated via the network to other luminaires in a particular group or zone.

The example of FIG. 7 mainly depicted a single system/source implementation, although several modifications to control additional luminaires/light sources were briefly discussed. The combined illumination and cleansing may be implemented in a variety of other source and controller implementations, particularly if intended for coordinated operations and/or monitoring thereof in a large installation, such as a hospital, rehabilitation facility, or nursing home.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus the following claims are hereby incorporated into the Detailed Description, with each claim standing on its own as a separately claimed subject matter.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. A luminaire, comprising:
  a general illumination light source capable of emitting visible light for a general illumination application in a volume in a vicinity of the luminaire;
  a laser light source configured to emit laser light having a first dominant wavelength in a visible light spectrum or in an infrared light spectrum;
  a light frequency up-converter, coupled to convert the laser light emitted by the laser light source to ultraviolet light of a second or higher order harmonic having a second dominant wavelength in an ultraviolet spectrum at or below 380 nanometers (nm), wherein:
    the light frequency up-converter comprises a harmonic generator configured to convert the laser light having the first dominant wavelength to the ultraviolet light of the second or higher order harmonic having the second dominant wavelength;
    the harmonic generator comprises a nonlinear metamaterial configured to exhibit:
      resonance for a frequency of the laser light having the first dominant wavelength from the laser light source and resonance for a harmonic frequency of the ultraviolet light of the second or higher order harmonic having the second dominant wavelength,
      substantial mode overlap between the frequency of the laser light from the laser light source and the harmonic frequency of the ultraviolet light of the second or higher order harmonic, and
      intrinsic nonlinear material or phase matching; and
  an optical element coupled to the light frequency up-converter to distribute the ultraviolet light for a cleansing application in the volume in the vicinity of the luminaire.

2. The luminaire of claim 1, wherein the nonlinear metamaterial comprises:

a gold split resonator structure;

a gold cross bar structure; or an all dielectric cylinder structure.

3. The luminaire of claim 1, wherein the nonlinear metamaterial includes a topological metamaterial.

4. The luminaire of claim 1, wherein the light frequency up-converter further comprises:

an additional laser light source configured to emit laser light having a third dominant wavelength in the visible light spectrum or in the infrared light spectrum; and an optical mixer coupled to receive and mix light from the laser light source and the additional laser light source to produce the ultraviolet light having the second dominant wavelength in the ultraviolet spectrum at or below 380 nm.

5. The luminaire of claim 4, wherein the optical mixer comprises a nonlinear crystal or a second nonlinear metamaterial.

6. The luminaire of claim 1, wherein the ultraviolet light has the second dominant wavelength in a range of from 180 nm to 380 nm.

7. The luminaire of claim 1, wherein the ultraviolet light has the second dominant wavelength in a range of from 200 nm to 225 nm.

8. The luminaire of claim 1, wherein the ultraviolet light has the second dominant wavelength in a range of from 207 nm to 222 nm.

9. The luminaire of claim 1, wherein the optical element comprises a beam shaping lens configured to disperse the ultraviolet light about a target region of the volume in the vicinity of the luminaire.

10. The luminaire of claim 1, wherein the optical element comprises a variable optical beam deflector configured to scan the ultraviolet light across a target region of the volume in the vicinity of the luminaire.

11. The luminaire of claim 1, wherein:

the general illumination light source includes one or more solid state lighting devices.

12. The luminaire of claim 11, wherein:

the one or more solid state lighting devices include one or more red, green, blue, or white light emitting diodes.

13. A cleansing lighting device, comprising:

a laser light source configured to emit laser light having a first dominant wavelength in a visible light spectrum or in an infrared light spectrum;

a light frequency up-converter, coupled to convert the laser light emitted by the laser light source to ultraviolet light of a second or higher order harmonic having a second dominant wavelength in the ultraviolet spectrum at or below 380 nanometers (nm), wherein:

the light frequency up-converter comprises a harmonic generator configured to convert the laser light having the first dominant wavelength to the ultraviolet light of the second or higher order harmonic having the second dominant wavelength;

the harmonic generator comprises a nonlinear metamaterial configured to exhibit:

resonance for a frequency of the laser light having the first dominant wavelength from the laser light source and resonance for a harmonic frequency of the ultraviolet light of the second or higher order harmonic having the second dominant wavelength, substantial mode overlap between the frequency of the laser light from the laser light source and the harmonic frequency of the ultraviolet light of the second or higher order harmonic, and intrinsic nonlinear material or phase matching; and an optical element coupled to the light frequency up-converter to distribute the ultraviolet light for a cleansing application in a volume in a vicinity of the cleansing lighting device.

14. The cleansing lighting device of claim 13, wherein the light frequency up-converter further comprises:

an additional laser light source configured to emit laser light having a third dominant wavelength in the visible light spectrum or in the infrared light spectrum; and an optical mixer coupled to receive and mix light from the laser light sources and the additional laser light source to produce the ultraviolet light having the second dominant wavelength in the ultraviolet spectrum at or below 380 nm.

15. The cleansing lighting device of claim 13, wherein the ultraviolet light has the second dominant wavelength in a range of from 200 nm to 380 nm.

16. The cleansing lighting device of claim 13, wherein the ultraviolet light has the second dominant wavelength in a range of from 200 nm to 225 nm.

17. The cleansing lighting device of claim 13, wherein the ultraviolet light has the second dominant wavelength in a range of from 207 nm to 222 nm.

18. The cleansing lighting device of claim 13, wherein the nonlinear metamaterial includes a topological metamaterial.

* * * * *